(12) United States Patent
Marak et al.

(10) Patent No.: US 8,157,782 B2
(45) Date of Patent: Apr. 17, 2012

(54) IV INFUSION CARRIER PACK

(75) Inventors: Joseph J. Marak, Whitewater, CO (US);
Carston R. Calkin, Tualatin, OR (US)

(73) Assignee: Skedco, Inc., Tualatin, OR (US)

( * ) Notice: Subject to any disclaimer, the term of this patent is extended or adjusted under 35 U.S.C. 154(b) by 126 days.

(21) Appl. No.: 12/870,528

(22) Filed: Aug. 27, 2010

(65) Prior Publication Data

US 2010/0324532 A1    Dec. 23, 2010

Related U.S. Application Data

(62) Division of application No. 11/807,633, filed on May 30, 2007, now abandoned.

(51) Int. Cl.
*A61B 19/00* (2006.01)

(52) U.S. Cl. ............ 604/408; 604/142; 604/410

(58) Field of Classification Search ............ 604/113, 604/172, 174, 262–263, 317, 327, 345, 403, 604/408, 410, 93.01, 131, 145, 142
See application file for complete search history.

(56) References Cited

U.S. PATENT DOCUMENTS

| | | | |
|---|---|---|---|
| 2,766,907 A * | 10/1956 | Wallace, Jr. ............ | 222/94 |
| 4,551,136 A * | 11/1985 | Mandl ............ | 604/141 |
| 4,804,367 A | 2/1989 | Smith et al. | |
| 5,053,011 A * | 10/1991 | Strobel et al. ............ | 604/142 |
| 5,279,589 A | 1/1994 | Feldman | |
| 5,295,964 A | 3/1994 | Gauthier | |
| 5,368,569 A * | 11/1994 | Sanese ............ | 604/113 |
| 5,700,257 A * | 12/1997 | Minick et al. ............ | 604/408 |
| 5,738,657 A * | 4/1998 | Bryant et al. ............ | 604/145 |
| 5,789,368 A | 8/1998 | You et al. | |

\* cited by examiner

*Primary Examiner* — Tatyana Zalukaeva
*Assistant Examiner* — Benedict L Hanrahan
(74) *Attorney, Agent, or Firm* — Stoel Rives LLP

(57) ABSTRACT

An IV infusion bag carrier pack is arranged as a substantially hollow, flexible bag having an interior that is divided into two interior compartments by a flexible, heat permeable divider panel, one interior compartment being arranged to receive and confine an IV fluids bag and the other interior compartment arranged to receive and confine the inflatable pressure cuff member of a blood pressure apparatus, whereby an IV fluids bag contained in the first pocket may be selectively pressurized by inflation of the blood pressure cuff contained in the second pocket whereby selectively controlled infusion delivery of IV fluids contained in the carrier pack apparatus may be continuously maintained irrespective of the relative disposition of the carrier pack apparatus and patient during treatment, extrication and rescue in the field, and transport to a medical facility.

8 Claims, 4 Drawing Sheets

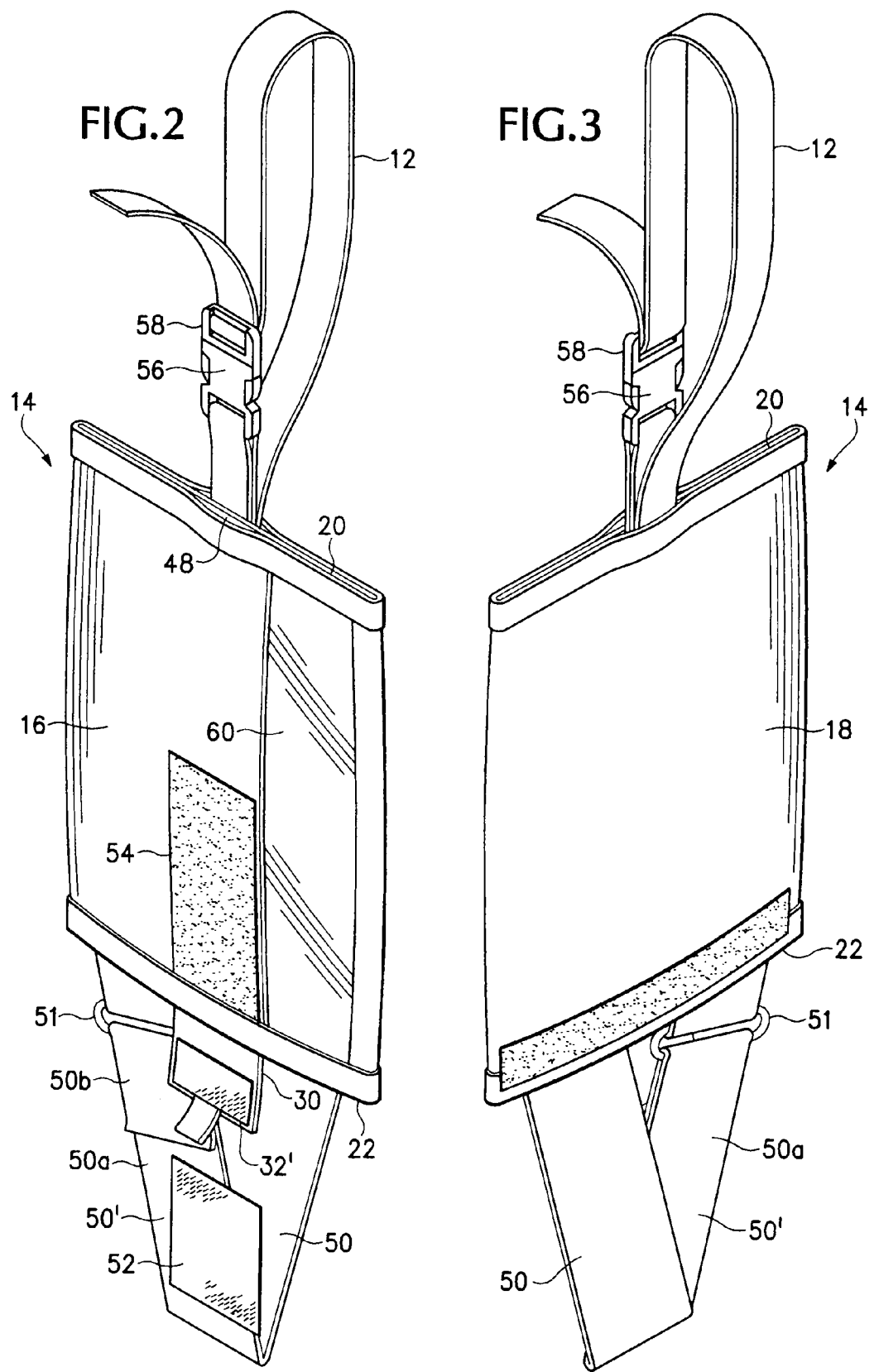

IV INFUSION CARRIER PACK

RELATED APPLICATIONS

This application is a divisional application of U.S. patent application Ser. No. 11/807,633, filed May 30, 2007 which is incorporated herein by reference.

BACKGROUND OF THE INVENTION

This invention relates generally to intravenous fluids bags used in emergency medical situations in the field, and more particularly to a carrier pack apparatus arranged to protectively hold and carry an IV fluids bag and selectively apply pressure and heat or cold to the IV bag during dispensing to a patient to assure that a positive infusion of proper temperature fluids to a patient is continuously maintained irrespective of the relative disposition of the IV bag and the patient during treatment and rescue procedures in field situations in combat, emergency extrications and rescue operations and transport of the patient to a medical facility.

As the average person is likely to be aware, it is common and necessary that oftentimes when a person is injured it is important that he receive intravenous fluids as soon as practicable. Most individuals have seen examples of patients connected to IV fluids bags by catheter tube and will have noticed that the fluid bag is typically held in an elevated position above the patient either by a support hook structure or by a person holding the bag in hand. In this manner, the flow of the IV fluids through the catheter tube to the patient is assured by the force of gravity. Often however, particularly in combat, extrication and rescue situations, it is not possible to retain an IV bag in an elevated position above the patient, and consequently the IV bag must be placed on the patient's body or stretcher where IV fluid transfer is either greatly slowed or effectively stopped.

Also, as is well understood by those skilled in the art, combat and rescue situations occur in widely divergent temperature situations which are often at odds with the patient's needs while being tended in emergency medical circumstances. Examples of such temperature situations are the extremely hot, desert combat situations of places like Iraq and Afghanistan, and mountain rescue situations of hikers, etc. in subfreezing temperatures high up on mountains. Those skilled in the art will immediately recognize that it is less than desirable to infuse an injured patient in hot, desert climates with fluids that have warmed prior to use by their storage in the extremely hot desert environment. By the same token, it is undesirable to infuse a hypothermic patient with fluids that have been chilled as they have been transported to the scene of a mountain rescue. Indeed, in the above cases, the infusion of fluids is often necessary to help stabilize the body temperature against the heat or chill of the surrounding environment.

Therefore, it can be seen that a need exists for an IV infusion bag carrier pack that is arranged to be conveniently and protectively carried in hands-free condition supported on a combat or military or rescue personnel, and operable to provide pressurized, temperature-controlled infusion of the contents of an IV fluids bag to a patient irrespective of the relative positioning of the carrier pack and the IV bag contained therein relative to the patient.

SUMMARY OF THE INVENTION

In its basic concept this invention provides an IV infusion bag carrier pack arranged as a substantially hollow, flexible bag, closed at one end and divided into two interior compartments by a flexible, heat permeable divider panel, one interior compartment arranged to receive and confine an IV fluids bag and the other, adjacent interior compartment arranged to receive and confine the inflatable pressure cuff member of a blood pressure apparatus and, if desired, a selected heat-generating packet or cold-generating packet for disposition immediately adjacent the divider panel separating the two compartments, whereby an IV fluids bag contained in the first pocket may be selectively heated or cooled during transport and dispensing and the blood pressure cuff may be inflated to a selected pressure within the second compartment to pressurize the IV fluids bag in the first compartment as needed to maintain a desired, uninterrupted infusion of fluid from the IV fluids bag to a catheterized patient.

It is by virtue of the foregoing concept that the principle objective of this invention is achieved; namely, the provision of an IV infusion bag carrier apparatus of the class described which protectively carries a selected intravenous fluids bag and inflatable blood pressure apparatus in hand-free condition supported on a personnel during transport between used and which in use maintains an IV fluids bag in a predetermined stated of pressurization for continuous infusion of the fluids to a catheterized patient during extrication, emergency treatment and transport of the patient to a medical facility.

Another object and advantage of the present invention is the provision of an IV infusion bag carrier apparatus of the class described which is arranged to hold a selected heat or cold-generating package adjacent the IV fluids bag to respectively heat or cool the IV fluids contained in the bag in order to maintain optimal temperature of the fluids to be delivered to a patient irrespective of the ambient air temperature of the surrounding environment in the field.

Another object and advantage of the present invention is the provision of an IV infusion bag carrier apparatus of the class described which provides an insulated carrier bag to minimize the effects of ambient air temperatures on the interior confines of an IV fluids bag contained in an interior compartment of the apparatus, for more effective control of the temperature of intravenous fluids to be delivered to a patient.

Another object and advantage of the present invention is the provision of an IV infusion bag carrier apparatus of the class described which is arranged to be worn on a personnel by a strap member arranged to position the carrier bag member adjacent the torso area of the personnel during carrying, whereby if desired, the carrier apparatus may be disposed adjacent the wearer's body beneath overlying clothing in order to utilize the wearer's body heat for controlling the temperature of the Iv fluids bag carried in the interior compartment of the carrier apparatus.

A further object and advantage of the present invention is the provision of an IV infusion bag carrier apparatus of the class described which includes a transparent window panel on an exterior wall of the bag member for viewing through the transparent window the fluid level of an IV fluids bag contained in the interior confines of the carrier apparatus.

A still further object and advantage of the present invention is the provision of an IV infusion bag carrier apparatus of the class described which is arranged to facilitate removal and installation of an IV fluids bag in the carrier apparatus without requiring disconnection of the catheter tube from the IV fluids bag.

A yet further object and advantage of the present invention is the provision of an IV infusion bag carrier apparatus of the class described which is of simplified construction for economical manufacture and reliability of use.

BRIEF DESCRIPTION OF THE DRAWINGS

FIG. 2 is a front perspective view of the IV infusion bag carrier pack apparatus in an open condition preliminary to provision of an IV fluids bag and a blood pressure cuff member.

FIG. 3 is a rear perspective view of the apparatus of FIG. 2 as seen from the opposite direction in FIG. 2.

DESCRIPTION OF THE PREFERRED EMBODIMENT

Figure 1:
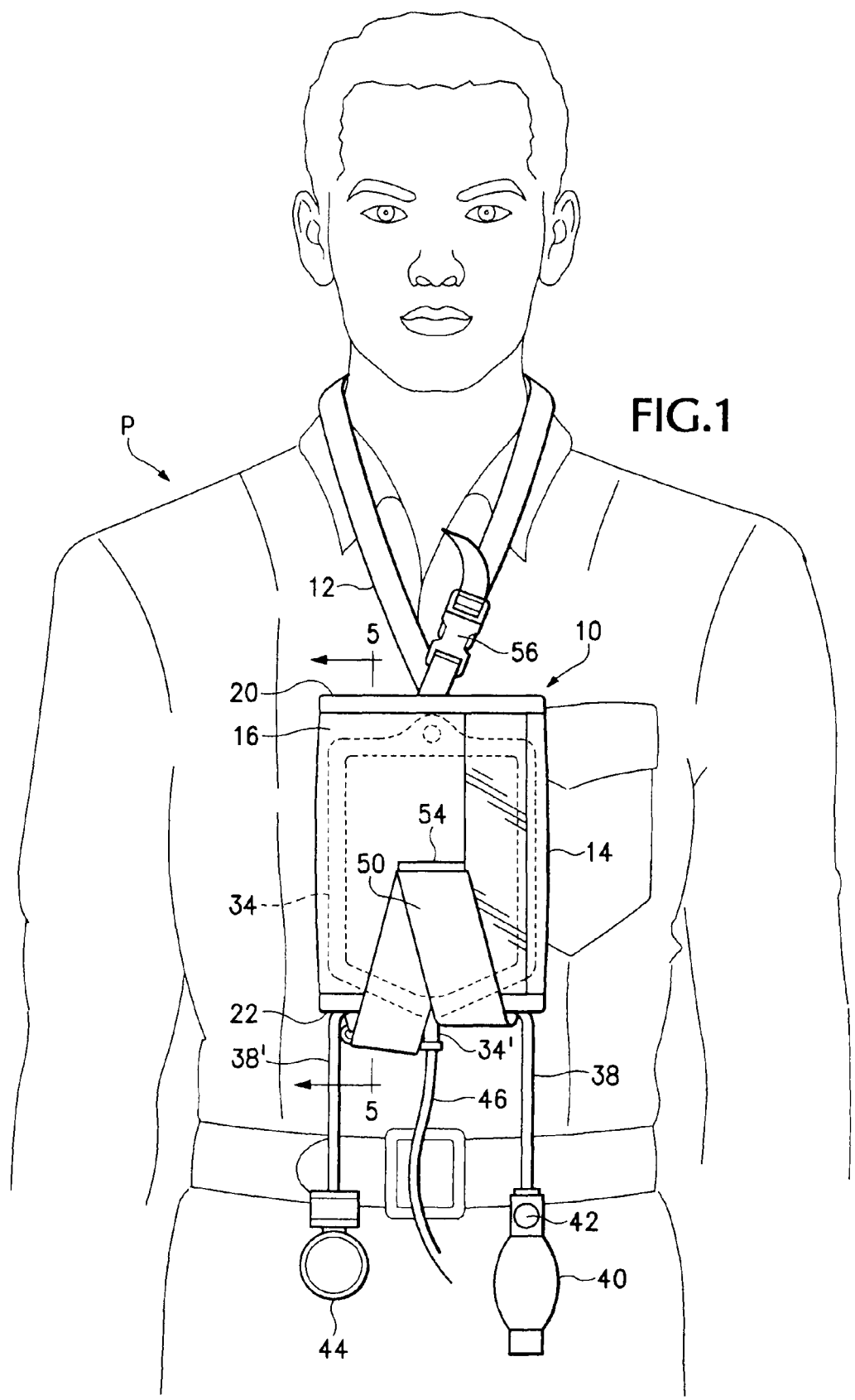
FIG. 1 is a fragmentary, front elevational view of an IV infusion bag carrier pack apparatus embodying features of this invention being carried in a supported condition overlying the torso area of a wearing personnel, the apparatus being shown in condition for infusion delivery of IV fluids to a catheterized patient.

FIG. 1 illustrates an IV infusion pack 10 embodying features of the present invention in use hanging by a neck-encircling strap member 12 on a medical or rescue personnel P. Alternatively, the apparatus may be similarly supported on the patient himself, as may be necessitated in extrication operations or as may be desired so that rescue personnel are not encumbered in their activities and movements by a need to carry an IV bag connected to the patient.

In its preferred form illustrated herein, an IV infusion pack 10 embodying features of this invention comprises a longitudinally elongated, hollow bag member 14 formed of flexible but generally non-elastic fabric material such as nylon, gortex, canvas or other selected fabric material. As illustrated the elongated bag member is preferably formed with a front wall panel 16 and a rear wall panel 18, each panel 16, 18 preferably including an intermediate insulation layer 19, the bag member having a substantially closed first longitudinal terminal end 20 and a substantially open second longitudinal terminal end 22, together defining a substantially hollow, insulated bag enclosure having an enclosed interior cavity which is substantially open through said second, open end 22 of the bag.

Figure 5:
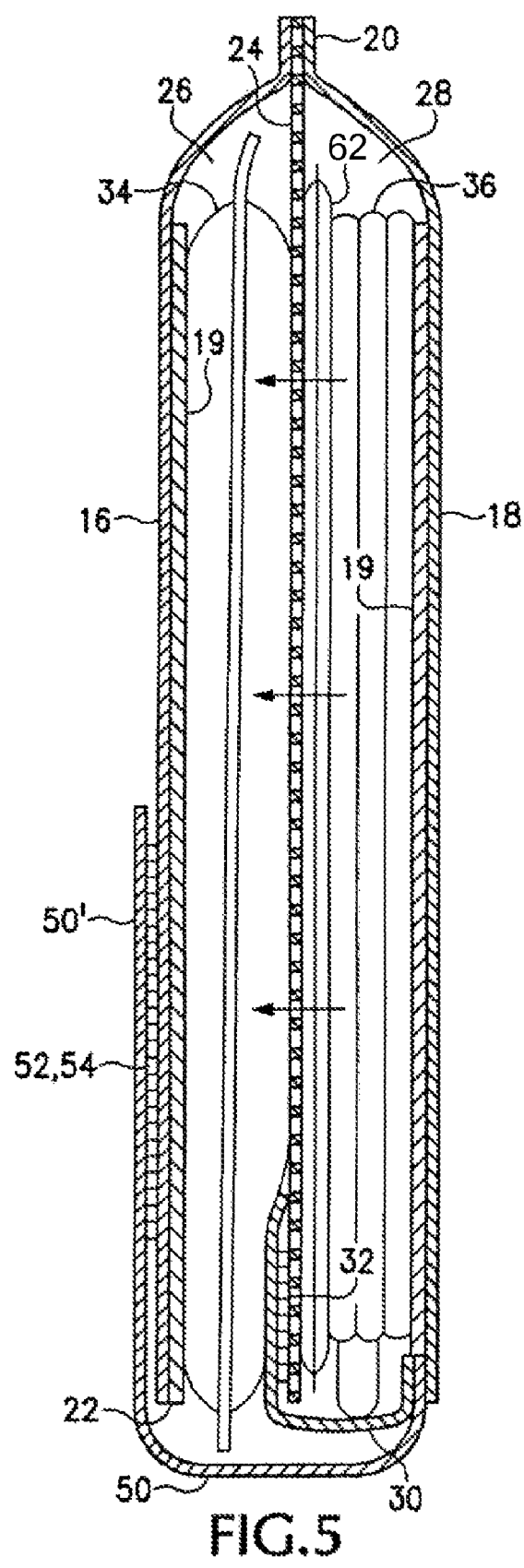
FIG. 5 is a vertical sectional view of the IV infusion bag carrier pack apparatus taken along the line 5-5 in FIG. 1.

As seen best in FIG. 5, the hollow bag member includes a generally flexible, heat-permeable divider panel 24 secured within the hollow interior cavity of the bag and arranged to divide the interior cavity into a first, front, longitudinally-elongated interior compartment or pocket 26 and a second, rear, longitudinally elongated interior compartment or pocket 28, each of the separate pockets 24, 26 being open to the open second end 22 of the bag member. This divider panel member preferably comprises a sheet of flexible, non-elastic mesh or net-type perforate fabric material having a plurality of openings therethrough for minimal restriction of temperature variations and heat transfer from one interior pocket to the other. The perforate fabric material may be of any suitable type, such as nylon, synthetic thermoplastic resin, metal mesh, natural fabric or other as may be desired, and is preferably white or light in color so that it provides a suitable background for viewing of the numbers and indicia on an IV fluids bag contained in the front pocket. A rear pocket closure flap member 30 is secured to the rear wall 18 of the bag and arranged to releasably overlie the open end of the rear pocket 28. The closure flap member 30 is releasably secured to the divider panel member 24 as by a hook and loop type fastener apparatus 32 having a selected one of corresponding interengaging hook and loop components 32' secured on the closure flap member 30 and divider panel 24 respectively, as shown in FIG. 5.

Figure 4:
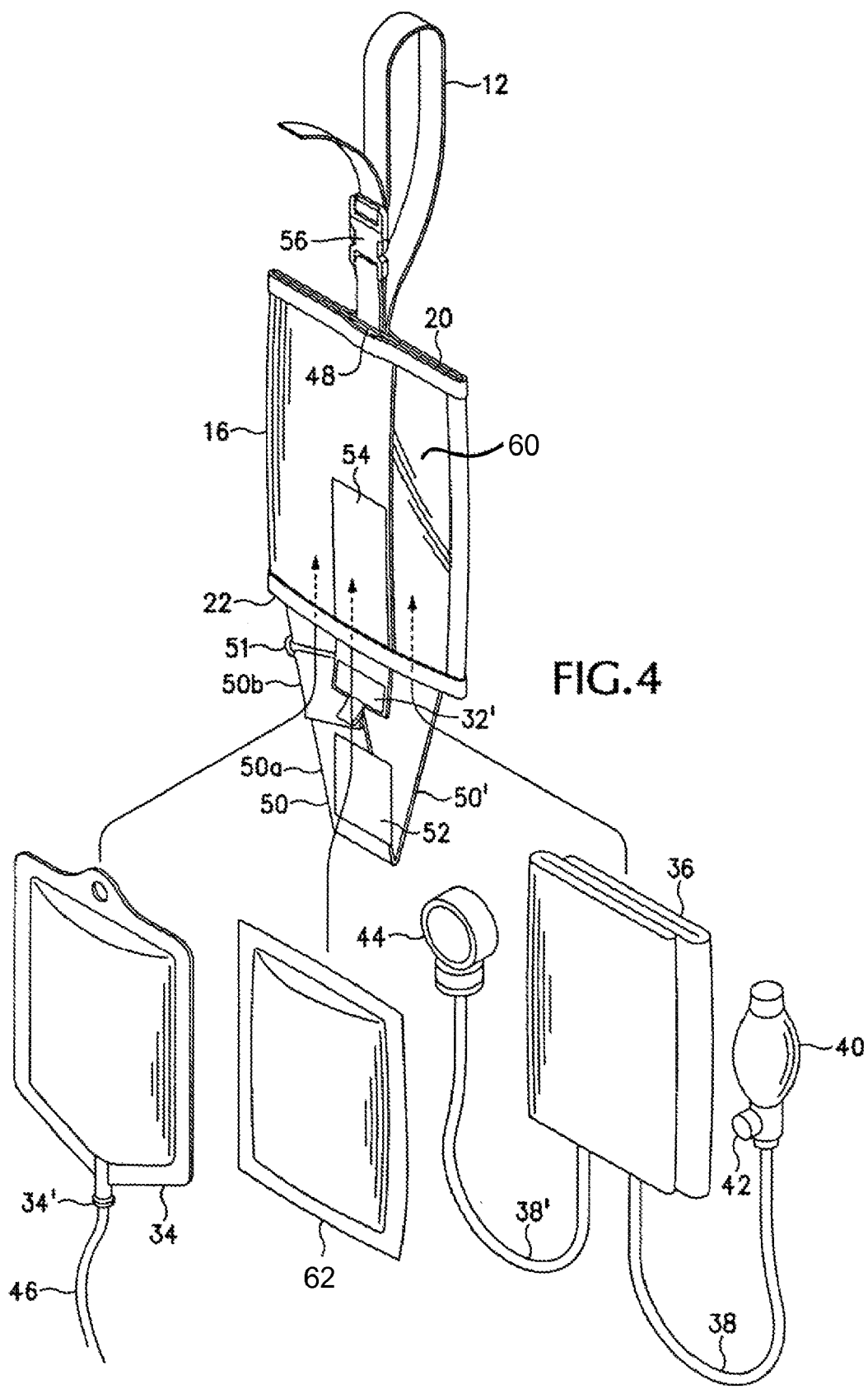
FIG. 4 is a fragmentary, exploded front perspective view of the carrier pack apparatus of FIG. 2 showing the installation of an IV fluids bag and blood pressure cuff apparatus into the first and second interior pockets, respectively, of the carrier pack.

As will also be readily evident in viewing FIGS. 4 and 5 of the drawings, the IV pack 10 of this invention is arranged and dimensioned to permit the front interior pocket 26 to receive and closely and snugly confine within its interior a selected, filled flexible IV fluids bag 34, and to permit the rear pocket 28 to receive and closely confine within its interior an inflatable blood pressure cuff 36 in a folded condition. As will be understood, the closure flap 30 is arranged to permit the tube 38 or tubes 38' for the inflation bulb 40, pressure release valve 42 and pressure gauge 44 of the blood pressure apparatus to extend out of the rear pocket 28 and through the open end 22 to the outside of the bag member.

The IV bag is positioned in the front pocket so that its outlet end fitting 34' is disposed adjacent the open end 22 of the bag for connection of a flexible IV tube 46, in conventional manner, for communicating fluids to a catheter (not shown) inserted in the patient as is well understood in the medical art. Also, an opening 48 may if desired also be provided through the first, closed end 20 of the bag for communication with the interior of the front pocket 26. In this manner, if it is desired or needed for a particular purpose, the IV bag may be placed into the front pocket in an inverted condition, for extension of the IV bag outlet fixture 34' and tube 46 through the opening 48 as will be understood.

As also shown in the drawings, the IV pack of this invention includes means for releasably and adjustably closing the second, open longitudinal end 22 of the bag. In the particular embodiment illustrated herein, this is accomplished by the provision of a bag closure flap member shown herein in the form of a generally V-shaped flap member 50 having legs forming the open end of the V-shape secured to the rear wall 18 of the bag. The flap member is arranged to overlie and lap over the open end 22 of the bag for releasable securement of the opposite, free, closed outer end 50' of the V-shaped flap member to the front wall panel 16 of the bag.

In this regard, the free, outer end portion 50' of the closure flap member 50 mounts a selected length of one component 52 of a hook and loop type fastener and the front wall 16 of the bag mounts a selected length of the corresponding component 54 of the hook and loop type fastener. This arrangement allows the closure flap member 50 to overlie and securely close the open end of the IV pack to snugly confine a full IV bag contained in the front interior pocket. Then if needed or desired, the closure flap member may be readjusted periodically as might be required to continue to snugly confine the IV bag as its fluid contents are continuingly depleted, as will be apparent to those skilled in the art.

Another important feature of a bag closure flap member, as represented in the embodiment of the V-shaped flap member 50 illustrated herein, is that it accommodates passage of the pressure cuff tubes 38, 38' and the IV bag catheter tube 46 out of the interior confines of the IV pack when the closure flap member 50 is operatively secured, as is clearly shown in FIG. 1. Clearly, however, other configurations of bag end closure arrangements suitable for the purpose may alternatively be provided, as will be evident to those skilled in the art.

For example, as is shown in the particular, preferred embodiment illustrated herein, the V-shaped closure flap member 50 preferably includes one leg 50a having an inner end portion 50b that is arranged for releasable attachment to the rear wall 18 adjacent the open end 22 of the bag. In the particular embodiment illustrated, the rear panel 18 mounts a metal ring member 51 arranged to receive the inner end portion 50b of the one leg 50a of the V-shaped strap member. In turn, the inner end portion mounts corresponding hook and loop components 51a, 51b respectively of a hook and loop type fastener apparatus arranged to secure the end portion together in a folded condition shown with the ring member 51 captured therebetween.

In this manner, when it is necessary to replace an IV fluids bag after its fluid contents have been depleted, the outer free end 50' of the closure front member 50 is released from its hook and loop connection to the fastener 54 on the front wall 16, permitting the open end 22 of the bag to be opened to expose the depleted fluids bag in the first pocket. The inner end portion 50b of the V-shaped closure flap member 50 is then disconnected from its captured engagement with metal securement ring member 51, thus freeing the outlet fitting 34' and IV tube 46 from the surrounding V-shaped strap closure arrangement and permitting separation of the tube and outlet fitting from the carrier bag without disconnection from the IV fluids bag 34 also being removed therewith. This greatly facilitates fluids bag removal and replacement operations, as those skilled in the art will readily recognize.

As previously mentioned, and as shown in the drawings, the IV pack of this invention also mounts a neck or shoulder carrier strap member 12 by which the IV pack can be carried in a convenient, non-encumbering, hands-free suspended condition on a rescue personnel. While this arrangement obviously allows the IV pack to be carried and used without encumbering the hands of the rescue personnel, it also affords other advantages that will be readily evident to those skilled in the art.

In the embodiment illustrated, the strap 12 is secured to the bag for extension, as shown, from the first, closed end 20 whereby the IV pack is supported in the hanging condition shown. The strap member 12 may, as shown, be provided with a quick release arrangement, such as interengaging buckle apparatus 56, to facilitate removal of the IV pack from the wearer, as may be desirable in situations for example, where the wearer is wearing a helmet. The strap member may also as shown be provided for adjustment of its length, as by friction adjustment member 58 shown.

As seen in FIGS. 1, 2 and 4 of the drawings, the front wall 16 of the IV pack includes means for viewing an IV fluids bag confined within the interior of the front pocket 26 of the bag. In the particular embodiment illustrated, the front wall 16 is formed with a longitudinally extending viewing window 60 through the front wall. This viewing window is preferably covered by a cover sheet of transparent material, such as clear plastic, secured to the front wall. In this manner, the level of the fluid contained in the IV bag 34 can be visually seen and monitored continuously at a glance.

From the foregoing it will be understood that in preparation of use, a blood pressure cuff 36 is folded and inserted into the rear pocket 28 with its tube 38, (or tubes 38, 38'), extended out of the top of the rear pocket and the open end 22 of the IV pack. If desired, a selected heat-generating or cold-generating packet 62, well known in the art, may be placed in the rear pocket between the blood pressure cuff and the divider panel and activated, so that an IV bag contained in the front pocket will be heated or cooled as desired for optimal infusion to the patient. The rear pocket closure flap 30 is then closed to secure the cuff and heat or cold generating packets within the confines of the pocket 28. The IV pack is then ready to receive a selected IV fluids bag 34 when the pack is to be readied for use for a rescue operation or other medical endeavor.

A selected IV fluids bag 34 is then inserted into the front pocket 26 with its outlet fixture 34' disposed at the open end 22 of the bag (or alternatively, in registry with the opening 48 through the closed end 20 of the bag). The bag closure flap member 50 is then secured in condition overlying and snugly closing the open end 22 of the bag, the IV fitting 34' extending through the opening through the closure flap member. The carrier strap 12 of the IV pack may then be slung about a wearer's neck or over his shoulder and the pack carried in suspended manner without interfering with the wearer's hands or activities.

When needed, and with a catheter inserted in a patient and the IV tube 46 connected to the catheter and IV bag, the IV is started in normal manner well known to those skilled in the medical art. The blood pressure cuff 36 may then be inflated by operation of bulb 40 to a predetermined pressure as witnessed by gauge 44 to expand the cuff in the rear pocket 28 and thereby apply pressure against the IV fluids bag 34 contained in the front pocket 26. This increased pressure on the snugly confined IV bag 34 assures positive and uninterrupted delivery of fluids irrespective of the disposition of the IV pack relative to the patient. Also, should the patient require, the blood pressure cuff can be inflated to a higher predetermined pressure in order to provide rapid infusion of the IV fluid if needed by the patient in a given situation.

Also it will be readily apparent that, with the IV pack secured by the neck or shoulder strap 12, whether on the rescue personnel or the patient himself, the IV pack may be supported thusly under the wearer's jacket to facilitate warming of the IV fluids contained in the IV pack by the radiant heating from the wearer's body. Further warming of the fluids can be obtained by extending the IV tube through the wearer's sleeve. It will also be apparent that separate IV packs can be suspended from each shoulder of the wearer and positioned in the area of the armpits for warming.

If the IV pack is hung or otherwise supported in positioned elevated above the patient, as when transporting the patient in ambulance or other vehicle, the IV fluids may be delivered by gravity feed, without need of pressurizing the cuff if so desired. Also, it will be appreciated that, with the IV pack of this invention secured to the patient himself, the unattended delivery of fluids is assured even during extrication procedures which may be lengthy, complex and require manipulating the patient into vertical, rotated and other positions that would otherwise interfere with and complicate the delivery of IV fluids to the patient during such activities.

From the foregoing it will be readily apparent to those skilled in the art that many various changes other than those already discussed may be made in the size, shape, type, number and arrangement of parts described hereinbefore without departing from the spirit of this invention and the scope of the appended claims.

Having thus described our invention and the manner in which it may be used, we claim:

1. An IV infusion bag for protectively holding and pressurizing an IV fluids bag, the IV infusion bag comprising:
   a) a substantially hollow bag formed of flexible material, the bag having a substantially closed, first bag end and a substantially open, second bag end forming a substantially hollow bag enclosure having an enclosed interior cavity open through said second, open bag end;

b) a divider secured in said interior bag cavity to divide the interior cavity into a front interior pocket and a rear interior pocket, each pocket open to said open, second bag end;

c) an IV fluids bag in said front interior pocket;

d) a folded, inflatable blood pressure cuff in said rear interior pocket;

e) a rear pocket closure flap secured to a rear wall of the IV infusion bag and releasably secured to said divider to overlie and close said rear interior pocket to confine therein the folded, inflatable blood pressure cuff; and f) an IV infusion bag closure flap secured to the rear wall of the IV infusion bag and releasably secured to a front wall of the IV infusion bag to overlie the rear interior pocket and the front interior pocket to close the second, open bag end and confine therein the folded, inflatable blood pressure cuff and the IV fluids bag.

2. An IV infusion bag according claim 1, wherein said IV infusion bag closure flap includes a substantially V-shaped flag member having a pair of legs forming the open end of the V-shape, the legs secured to the rear wall of the IV infusion bag, at least one of said legs being secured releasably to the rear wall of the IV infusion bag, the V-shaped flag member having a free end arranged for releasable securement to the front wall, the flag member arranged to releasably overlie and close the open end of the bag member.

3. An IV infusion bag according to claim 2, wherein said V-shaped flag member includes an opening between said pair of legs, said opening for passage through the V-shaped flag member of a catheter tube connected to the IV fluids bag contained in said front pocket.

4. An IV infusion bag according to claim 1, further comprising an inflation tube of the blood pressure cuff contained in the rear interior pocket extending out of the rear interior pocket and through the IV infusion bag closure flap when the IV infusion bag closure flap closes the open, second bag end.

5. An IV infusion bag according to claim 1, further comprising a selected heat or cold-generating packet in said rear pocket, wherein the selected heat or cold-generating packet is located between the divider and the folded, inflatable blood pressure cuff.

6. An IV infusion bag according claim 1, further comprising a carrier strap member secured on said bag member and arranged to support the IV infusion bag carrier pack apparatus in a hanging condition.

7. A method for administering an IV fluid to a patient comprising:

a) providing a substantially hollow bag formed of flexible material, the bag having a substantially closed, first bag end and a substantially open, second bag end forming a substantially hollow bag enclosure having an enclosed interior cavity open through said second, open bag end wherein a divider secured in said interior bag cavity divides the interior cavity into a front interior pocket and a rear interior pocket, each pocket open to said open, second bag end;

b) inserting a folded, inflatable blood pressure cuff into said rear pocket;

c) releasably securing a free end of a rear pocket closure flap that has an opposing end secured to a rear wall of the bag to said divider to overlie and close said rear interior pocket and confine therein the folded, inflatable blood pressure cuff;

d) inserting an IV fluids bag into said front pocket;

e) releasably securing a free end of a bag closure flap that has an opposing end secured to the rear wall of the bag to a front wall of the bag to overlie the rear interior pocket and the front interior pocket to close the second, open bag end and confine therein the folded, inflatable blood pressure cuff and the IV fluids bag;

f) connecting the IV fluids bag to a patient to start flowing fluids from the IV fluids bag into the patient; and g) pressurizing the folded, inflatable blood pressure cuff to provide positive delivery of fluids to the patient irrespective of the disposition of the IV fluids bag relative to the patient.

8. A method for administering an IV fluid to a patient according to claim 7, further comprising:

inserting a heat-generating or a cold-generating packet into said rear pocket such that said heat-generating or cold-generating packet lies between said divider and said folded, inflatable blood pressure cuff.

\* \* \* \* \*